US012734211B2

(12) United States Patent
Ling et al.

(10) Patent No.: US 12,734,211 B2
(45) Date of Patent: Sep. 15, 2026

(54) USE OF POLYPEPTIDE IN DRUG FOR PREVENTING AND TREATING PNEUMONIA

(71) Applicants: ZHEJIANG ECHON BIOMEDICAL CO., LTD., Hangzhou (CN); NANNING GENLOCI BIOMEDICAL CO., LTD., Nanning (CN)

(72) Inventors: Jianqun Ling, Hangzhou (CN); Qingping Lin, Hangzhou (CN)

(73) Assignees: ZHEJIANG ECHON BIOMEDICAL CO., LTD., Hangzhou (CN); NANNING GENLOCI BIOMEDICAL CO., LTD., Nanning (CN)

( * ) Notice: Subject to any disclaimer, the term of this patent is extended or adjusted under 35 U.S.C. 154(b) by 691 days.

(21) Appl. No.: 18/024,783

(22) PCT Filed: May 12, 2021

(86) PCT No.: PCT/CN2021/093228

§ 371 (c)(1),
(2) Date: Mar. 6, 2023

(87) PCT Pub. No.: WO2022/048180

PCT Pub. Date: Mar. 10, 2022

(65) Prior Publication Data

US 2023/0330178 A1 Oct. 19, 2023

(30) Foreign Application Priority Data

Sep. 4, 2020 (CN) ......................... 202010925707.9

(51) Int. Cl.
*A61K 38/10* (2006.01)
*A61K 45/06* (2006.01)
*A61P 31/04* (2006.01)

(52) U.S. Cl.
CPC .............. *A61K 38/10* (2013.01); *A61K 45/06* (2013.01); *A61P 31/04* (2018.01)

(58) Field of Classification Search
CPC ......... A61K 38/10; A61K 45/06; A61P 31/04; A61P 11/00
See application file for complete search history.

(56) References Cited

U.S. PATENT DOCUMENTS

2021/0220432 A1* 7/2021 Ling ........................ A61K 9/06

FOREIGN PATENT DOCUMENTS

CN 108771028 A 11/2018
CN 111214644 A 6/2020

(Continued)

OTHER PUBLICATIONS

Mardirossian et al. In vitro and in vivo evaluation of BMAP-derived peptides for the treatment of cystic fibrosis-related pulmonary infections. Amino Acids. Sep. 2016;48(9):2253-60. doi: 10.1007/s00726-016-2266-4. Epub Jun. 6, 2016. PMID: 27270571 (Year: 2016).*

(Continued)

*Primary Examiner* — Randall L Beane

(74) *Attorney, Agent, or Firm* — Bayramoglu Law Offices LLC

(57) ABSTRACT

A use of a polypeptide in a drug for preventing and treating pneumonia is provided. The polypeptide may effectively prevent and treat pneumonia, and may also be added with another therapeutic agent, excipient, carrier, or auxiliary ingredient to prepare a drug with the polypeptide and the therapeutic agent as main active ingredients for preventing and treating pneumonia. The present invention further discloses a use of the polypeptide and a drug thereof in prevention and treatment of pneumonia. The drug has good inhibitory and treatment effects on pneumonia, may effec- (Continued)

tively act on pneumonia caused by pathogenic bacteria for effective prevention, and may also improve a treatment effect on pneumonia. Compared with the prior art, the polypeptide and the drug thereof have effects of high safety and no drug resistance, can effectively prevent and treat pneumonia, and have high-value application prospects.

6 Claims, 4 Drawing Sheets

Specification includes a Sequence Listing.

(56) References Cited

FOREIGN PATENT DOCUMENTS

| | | | |
|---|---|---|---|
| CN | 111375051 | A | 7/2020 |
| EP | 2944195 | A1 | 11/2015 |
| WO | 2017091734 | A2 | 6/2017 |

OTHER PUBLICATIONS

Colthorpe et al., The pharmacokinetics of pulmonary-delivered insulin: a comparison of intratracheal and aerosol administration to the rabbit. Pharm Res. Jun. 1992;9(6):764-8. doi: 10.1023/a:1015851521551. PMID: 1409359 (Year: 1992).*

Bodier-Montagutelli et al. Designing inhaled protein therapeutics for topical lung delivery: what are the next steps? Expert Opin Drug Deliv. Aug. 2018;15(8):729-736. doi: 10.1080/17425247.2018.1503251. Epub Jul. 27, 2018. PMID: 30025210 (Year: 2018).*

Daniels et al., Nebuliser systems for drug delivery in cystic fibrosis. Cochrane Database of Systematic Reviews 2013, Issue 4. Art. No. CD007639. DOI: 10.1002/14651858.CD007639.pub2 (Year: 2013).*

Hess et al., Medication nebulizer performance. Effects of diluent volume nebulizer flow, and nebulizer brand. Chest. Aug. 1996;110(2):498-505. doi: 10.1378/chest.110.2.498. PMID: 8697857 (Year: 1996).*

Lyczak et al., Lung infections associated with cystic fibrosis. Clin Microbiol Rev. Apr. 2002;15(2):194-222. doi: 10.1128/CMR.15.2.194-222.2002. PMID: 11932230; PMCID: PMC118069 (Year: 2002).*

Collins, Nebulizer therapy in cystic fibrosis: an overview. J R Soc Med. Jul. 2009;102 Suppl 1(Suppl 1):11-7. doi: 10.1258/jrsm.2009.s19003. PMID: 19605869; PMCID: PMC2711853 (Year: 2009).*

Pompilio et al., Potential novel therapeutic strategies in cystic fibrosis: antimicrobial and anti-biofilm activity of natural and designed α-helical peptides against *Staphylococcus aureus*, Pseudomonas aeruginosa, and Stenotrophomonas maltophilia. BMC Microbiol. Jul. 23, 2012;12:145. (Year: 2012).*

Tang Lin-Min, et al., Analysis of pathogen resistance and risk factors in ICU hospitalized patients with HAP, Practical Pharmacy And Clinical Remedies, 2016, pp. 367-370, vol. 19, No. 03.

Huang Fang, et al., Epidemiological characteristics of hospital-acquired pneumonia and prevention measures, Chinese Journal of Nosocomiology, 2018, pp. 2053-2055, vol. 28, No. 13.

Xiaobo Ying, et al., A survey of the aetiology of community-acquired pneumonia in adults in different seasons, Chinese Journal of Public Health Management, 2014, pp. 843-844,849, vol. 30, No. 6.

Michael Burk, et al., Viral infection in community-acquired pneumonia: a systematic review and meta-analysis, Eur Respir Rev, 2016, pp. 178-188, vol. 25.

T.C. Jyothi, et al., Napin from *Brassica juncea*: Thermodynamic and structural analysis of stability, Biochimica et Biophysica Acta, 2007, pp. 907-919, vol. 1774.

Dipesh Shah, et al., Thermodynamic parameters associated with guanidine HCI- and temperature-induced unfolding of bFGF, International Journal of Pharmaceutics, 1998, pp. 1-14, vol. 169.

Cui Xu, et al., Chemical and biological stability of vasoactive intestinal peptide, Chinese Journal of New Drugs, 2011, pp. 1922-1925, vol. 20, No. 19.

Mitchell J. Goldman, et al., Human β-Defensin-1 Is a Salt-Sensitive Antibiotic in Lung That Is Inactivated in Cystic Fibrosis, Cell, 1997, pp. 553-560, vol. 88.

Robert E. W. Hancock, et al., The role of cationic antimicrobial peptides in innate host defences, Trends in Microbiology, 2000, pp. 402-410, vol. 8, No. 9.

Mario Mardirossian, et al., In vitro and in vivo evaluation of BMAP-derived peptides for the treatment of cystic fibrosis-related pulmonary infections, Amino Acids, 2016.

Mario Mardirossian, et al., D-BMAP18 Antimicrobial Peptide Is Active In vitro, Resists to Pulmonary Proteases but Loses Its Activity in a Murine Model of Pseudomonas aeruginosa Lung Infection, Frontiers in Chemistry, 2017, pp. 1-9, vol. 5, Article 40.

Sambrook, et al., Molecular Cloning: A Laboratory Manual, 2001, Cold Spring Harbor Laboratory Press.

Chiau-Jing Jung, et al., Identification of potential therapeutic antimicrobial peptides against Acinetobacter baumannii in a mouse model of pneumonia, Scientific Reports, 2021, pp. 1-10, vol. 11, No. 7318.

Dmytro P. Yevtushenko, et al., Transgenic Expression of Antimicrobial Peptides in Plants: Strategies for Enhanced Disease Resistance, Improved Productivity, and Production of Therapeutics, Small Wonders: Peptides for Disease Control, 2012, pp. 445-458.

Sungtae Yang, et al., Structural analysis and mode of action of BMAP-27, a cathelicidin-derived antimicrobial peptide, Peptides, 2019, pp. 1-10, vol. 118, 170106.

Lee R. Haines, et al., Killing of Trypanosomatid Parasites by a Modified Bovine Host Defense Peptide, BMAP-18, PLOS Neglected Tropical Diseases, 2009, pp. 1-13, vol. 3, Issue 2, e373.

Ji Ling Qiu Shi Zhi, The Fenmu's Skin Antibacterial Liquid is great, what bacteria does it work against?, 2020.

* cited by examiner

Note: FIGS. 1A-1C correspond to rats in model evaluation group

Note: FIGS. 1D-1F correspond to rats in model evaluation group

Note: FIGS. 2A-2C are blank control group, model control group, and erythromycin group, respectively Note: FIGS. 2D-2F are budesonide group, low-dose polypeptide treatment group, and high-dose polypeptide treatment group, respectively Note: FIGS. 3A-3C are blank control group, model control group, and erythromycin group, respectively Note: FIGS. 3D-3F are budesonide group, low-dose polypeptide treatment group, and high-dose polypeptide treatment group, respectively Note: FIG. 3G is blank administration group

USE OF POLYPEPTIDE IN DRUG FOR PREVENTING AND TREATING PNEUMONIA

CROSS REFERENCE TO THE RELATED APPLICATIONS

This application is the national phase entry of International Application No. PCT/CN2021/093228, filed on May 21, 2021, which is based upon and claims priority to Chinese Patent Application No. 202010925707.9, filed on Sep. 4, 2020, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBNJZL093_Sequence_Listing.txt, created on Feb. 24, 2023, and is 660 bytes in size.

TECHNICAL FIELD

The present invention relates to the technical field of medicine, and in particular, to a use of a polypeptide in a drug for preventing and treating pneumonia.

BACKGROUND

Pneumonia is a common disease of a respiratory system. According to incidence places, the pneumonia can be divided into community-acquired pneumonia (CAP) and hospital-acquired pneumonia (HAP).

The CAP is a heterogeneous disease, also known as out-of-hospital acquired pneumonia. The CAP refers to an infectious pulmonary parenchymal inflammation affected outside a hospital, and is mostly caused by bacteria, viruses, fungi, and atypical pathogens, among which bacterial pneumonia is the most common among patients, is a lower respiratory tract infection in clinic, and is also one of the common diseases that seriously threaten human health.

The HAP, mostly caused by bacterial infections, attacks a patient who is not indicated of infection before admission but suffers from pneumonia in hospital after 48 hours (TANG Lin-min, LOU Juan-hua, HU Zhen-zhen. Analysis of pathogen resistance and risk factors in ICU hospitalized patients with HAP [J], Practical Drugs and Clinics, 2016, 19(03): 367-370.). The HAP has attracted wide attention from clinical and preventive scholars in recent years because of its characteristics such as strong transmission and easy aggravation of patients' illness and disease burden (HUANG Fang, CHEN Xing-feng, WANG Yan-ping. Epidemiological characteristics and preventive measure study of hospital acquired pneumonia [J]. Chinese Journal of Nosocomiology, 2018, 28(13): 2053-2055.).

YING Xiao-bo et al. reported simple pneumonia pathogen infections, with bacterial infections accounting for 31.81% and mixed infections accounting for 10.23%. After mixed infections and simple infections were combined, the bacterial infections accounted for 40.91%. It can be seen that the bacterial infections ranked first in pneumonia (YING Xiao-bo, WANG Dan-min, SONG Bo, LAN Da-bo. Etiological investigation of adult community-acquired pneumonia in different seasons [J]. China Public Health Administration, 2014, 30(06): 843-844+849.).

With progress of test methodology, multiple pathogens combined in the same patient may be tested out at the same time, increasing mixed infections were identified and found, and a mortality of CAP patients with combined bacterial infections was significantly higher than that of single pathogen infections (Burk M, El-Kersh K, Saad M, et al. Viral infection in community-acquired pneumonia: a systematic review and meta-analysis. EurRespir Rev, 2016, 25(140): 178-188.).

Existing drugs for treating pneumonia include erythromycin, budesonide, and the like. However, in processes of treatment with existing erythromycin and budesonide, more or less adverse reactions occur. The erythromycin is highly irritating, and may cause gastrointestinal reactions and liver damage by oral or intravenous administration. A large dose or long-term use of the erythromycin may lead to cholestasis, transaminase elevation, and the like. The erythromycin should not be used by pregnant women and patients with liver insufficiency, and should be used with caution by infants. The budesonide may cause oropharyngeal candidiasis or quick or slow allergic reactions, including rash, contact dermatitis, urticaria, angioneurotic edema and bronchospasm. In addition, drug resistance of pneumonia treatment has become an increasingly concerned global issue.

Therefore, it is extremely urgent to develop a drug preparation with a wide range of actions against main pathogens of pneumonia and without drug resistance and adverse reactions, so as to play an important role in initial treatment of pneumonia.

Antimicrobial peptides are a kind of basic peptides, generally composed of about 12 to 50 amino acids. The antimicrobial peptides have broad-spectrum antibacterial properties, can inhibit or kill bacteria, fungi, viruses, parasites, and tumor cells, and can promote wound healing. Moreover, the antimicrobial peptides can also act as immune activation molecules, regulate functions of a body's immune system, enhance a body's ability of clearing pathogens, neutralize bacterial endotoxin LPS, reduce release of inflammatory cytokines, and slow down tissue damage caused by inflammatory reactions. Although conventional antibiotics have obvious antibacterial effects, most of them resist microorganisms by hindering synthesis of bacterial cell walls, inhibiting synthesis of proteins, affecting metabolisms of nucleic acid and folic acid, and the like. The microorganisms can easily change their metabolic pathways through gene mutation, and then become resistant to the antibiotics. Compared with the antibiotics, the antimicrobial peptides have incomparable advantages in drug resistance. The antimicrobial peptides can form pores by interacting with microbial cell membranes, to affect osmotic pressure inside and outside cells, so as to cause cell death. Cell membrane structures of the microorganisms, which have evolved for hundreds of millions of years, do not change greatly in a short time, so antibacterial mechanisms of the antibacterial peptides are less prone to drug resistance in bacteria. Therefore, the antimicrobial peptides as antimicrobial ingredients are increasingly favored.

At present, an antimicrobial peptide database (APD, aps.unmc.edu) collects 3241 kinds of antimicrobial peptides, reports on antimicrobial activities of antimicrobial peptides in vitro are common, but reports on use of antimicrobial peptides in disease treatment are few. This is closely related to characteristics of antimicrobial peptides, conditions under which the antimicrobial peptides exert biological activities, and complex physiological environments of organisms.

A three-dimensional spatial structure of an antimicrobial peptide was mainly maintained by secondary bonds such as a hydrogen bond, a hydrophobic bond, a salt bond and Van der Waals' force (T. C. Jyothi, Sharmistha Sinha, Sridevi A.

Singh, A. Surolia, A. G. Appu Rao. Napin from *Brassica juncea*: Thermodynamic and structural analysis of stability [J]. BBA-Proteins and Proteomics, 2007, 1774(7).). Because the secondary bonds were all non-covalent bonds and were easily affected by pH, temperature, and the like in the environment, a domain of the protein polypeptide changed easily to change a conformation of the three-dimensional structure and cause denaturation, resulting in poor stability or loss of functions (Dipesh Shah, Thomas P. Johnston, Ashim K. Mitra. Thermodynamic parameters associated with guanidine HCl- and temperature-induced unfolding of bFGF [J]. International Journal of Pharmaceutics, 1998, 169(1).). For example, vasoactive intestinal peptide (VIP) was a linear cationic neuropeptide composed of 28 amino acids, and its stability was pH-dependent and temperature-dependent (CUI Xu, HAN Xuan, WANG Zhi-min, CAO De-ying, ZHENG Ai-ping. Study on chemical and biological stability of vasoactive intestinal peptide [J]. Chinese Journal of New Drugs, 2011, 20(19): 1922-1925.).

In addition, short half-life in vivo, easy inactivation by high salt ions, easy hydrolysis by proteases, and the like of the antimicrobial peptides also restrict their use in the pharmaceutical field. GOLDMAN et al. reported that antimicrobial activities of some antimicrobial peptides are negatively correlated with a concentration of Na+ in a solution, and the antimicrobial peptides are inactivated when a concentration of NaCl is 150 mmol/L (physiological salt concentration) (GOLDMAN M J, et al. Human beta-defensin-1 is a salt-sensitive antibiotic in lung that is inactivated in cystic fibrosis [J]. Cel,l 1997, 88(4): 553-560.) HANCOCK et al. reported that many factors can reduce activities of antimicrobial peptides, such as high concentrations of monovalent and divalent cations, polyanions, serum, apolipoprotein A-I, and proteases (HANCOCK R E W, DIAMOND G. The role of cationic antimicrobial peptides in innate host defences [J]. Trends in Microbiology, 2000, 8 (9): 402-410.).

BMAP-27, BMAP-28, and their short synthetic fragments belong to Cathelicidin family antibacterial peptides. Mardirossian et al. evaluated therapeutic effects of BMAP-derived peptides on cystic fibrosis-related pulmonary infections in vivo and in vitro, and results showed that polypeptides with high antibacterial activities in vitro did not show any therapeutic effect in an acute pulmonary infected mouse model (Mardirossian M, Pompilio A, Crocetta V, et al. In vitro and in vivo evaluation of BMAP-derived peptides for the treatment of cystic fibrosis-related pulmonary infections [J]. Amino Acids, 2016, 48 (9): 1-8.). Researchers attributed the reason to rapid degradation of polypeptides in face of pulmonary proteases. In order to improve the stability of a polypeptide, the researchers synthesized a D-type BMAP-18 polypeptide with protease resistance for further study. Similarly, D-BMAP-18 showed a strong antibacterial effect in vitro, but had no therapeutic effect when applied to mice with acute lung infection (Mardirossian M, Pompilio A, Degasperi M, Runti G, Pacor S, Di Bonaventura G and Scocchi M (2017) D-BMAP18 Antimicrobial Peptide Is Active In vitro, Resists to Pulmonary Proteases but Loses Its Activity in a Murine Model of *Pseudomonas aeruginosa* Lung Infection. Front. Chem. 5:40.).

The polypeptide of the present invention is an antibacterial polypeptide. The applicant was surprised to find that the polypeptide of the present invention had a relatively good antibacterial effect in animals, so the polypeptide can be used for producing a drug for preventing and treating pneumonia, with great application and research prospects. There is no report in the prior art that the polypeptide can be used for preventing and treating pneumonia.

SUMMARY

For the deficiencies of the prior art, the present invention provides a use of a polypeptide in a drug for preventing and treating pneumonia, and also provides a drug for preventing and treating pneumonia.

An amino acid sequence of the polypeptide in the present invention is SEQ ID NO: 1.

One aspect of the present invention provides a drug for preventing and treating pneumonia. An active ingredient of the drug includes a polypeptide.

The drug of the present invention may include the polypeptide as a sole therapeutic agent, which may alternatively be combined with another excipient, carrier, or auxiliary ingredient.

The drug of the present invention may further include one or more therapeutic agents, which may alternatively be combined with another excipient, carrier, or auxiliary ingredient.

Another aspect of the present invention provides a use of a polypeptide in a drug for preventing and treating pneumonia. The drug of the present invention is prepared from the polypeptide of the present invention as a main active ingredient, added with another pharmaceutically acceptable excipient, carrier, or auxiliary ingredient, and can be used for preventing and treating pneumonia.

Yet another aspect of the present invention provides a use of a polypeptide in a drug for preventing and treating pneumonia. The drug of the present invention is prepared from a combination of the polypeptide of the present invention and another therapeutic agent, added with another pharmaceutically acceptable excipient, carrier, or auxiliary ingredient, and can be used for preventing and treating pneumonia.

Preferably, the pneumonia includes community-acquired pneumonia.

Preferably, the preparation of the present invention further includes another excipient, carrier, or auxiliary ingredient.

A preparation of the present invention may be any one or a combination of an injection, lyophilized powder (for injection), a solid preparation, a spray, a solution, a suspension, an emulsion, a semi-solid preparation, a liquid preparation, tablets, capsules, enteric-coated tablets, pills, powder, granules, a sustained release or delayed release preparation, and the like.

Preferably, the preparation of the present invention may be administered by any one or a combination of oral administration, parenteral administration, topical administration, injection administration, inhalation administration, and mucosal administration.

Preferably, the pharmaceutical preparation provided by the present invention further includes one or more therapeutic agents.

Preferably, in the drug of the present invention, the therapeutic agent includes β-lactam/β-lactamase inhibitors (penicillins, cephalosporins), fluoroquinolones (moxifloxacin, gemifloxacin, and levofloxacin), carbapenems, erythromycin, budesonide, oseltamivir, azithromycin, oseltamivir, andrographolide, kalil dehydrographolidi succinatis, or combinations thereof.

To sum up, the present invention provides a use of a polypeptide in a drug for preventing and treating pneumonia, and also provides a drug prepared from the polypeptide or a combination of the polypeptide and another therapeutic agent as an effective ingredient, added with a pharmaceutically acceptable excipient, carrier, or auxiliary ingredient. Compared with the prior art, the effect of the polypeptide on bacterial pneumonia is better than that of existing drugs in use in the market. In addition, the polypeptide of the present invention does not develop drug resistance, can widely prevent and treat pneumonia, and has broad application prospects.

DETAILED DESCRIPTION OF THE EMBODIMENTS

Figures 1A, 1B, 1C:
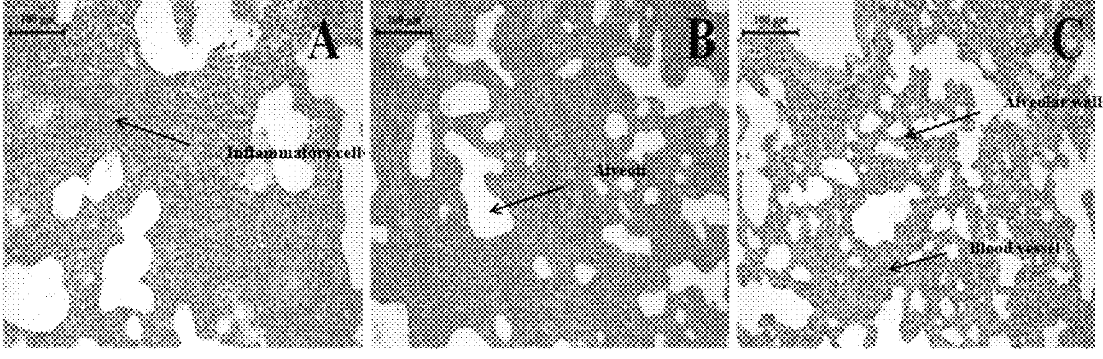
FIGS. 1A-IF are diagrams of pathological changes in lungs of model animals.
Figures 1D, 1E, 1F:
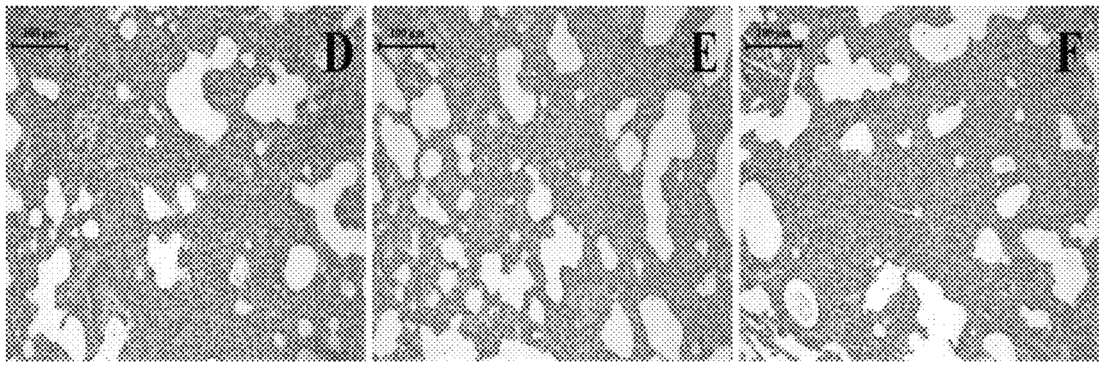
Figures 2A, 2B, 2C:
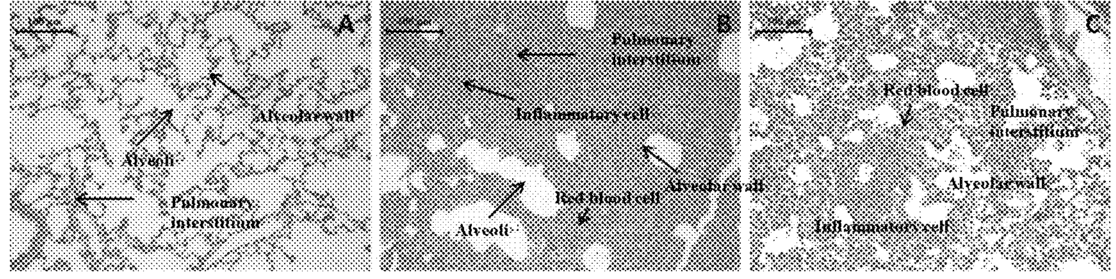
FIGS. 2A-2F are lung test diagrams of each test group on D4 day.
Figures 2D, 2E, 2F:
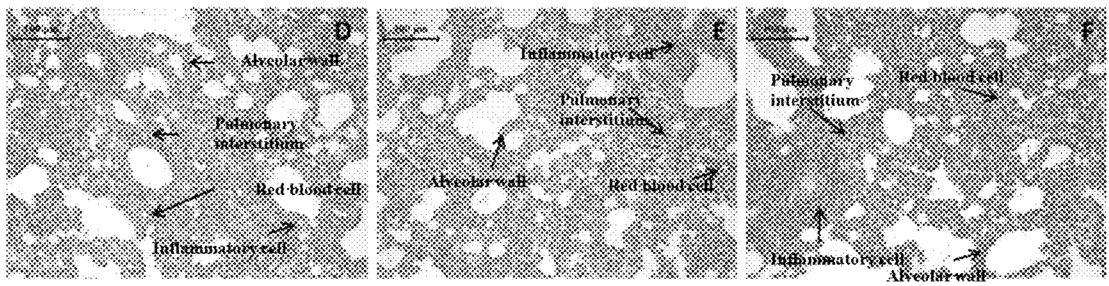
Figures 3A, 3B, 3C:
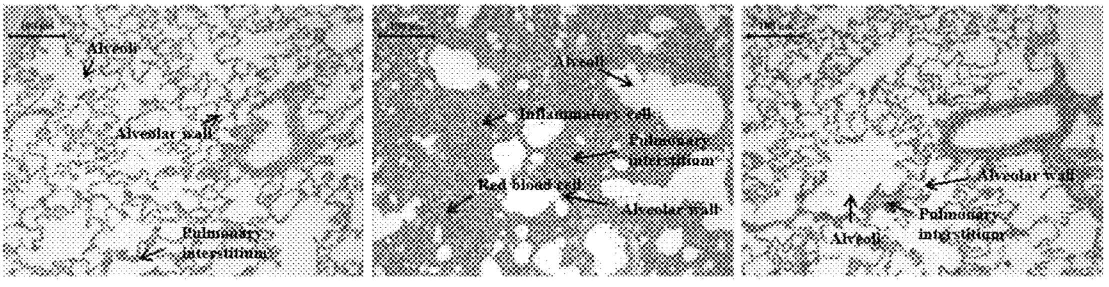
FIGS. 3A-3G are lung test diagrams of each test group on D8 day.
Figures 3D, 3E, 3F:
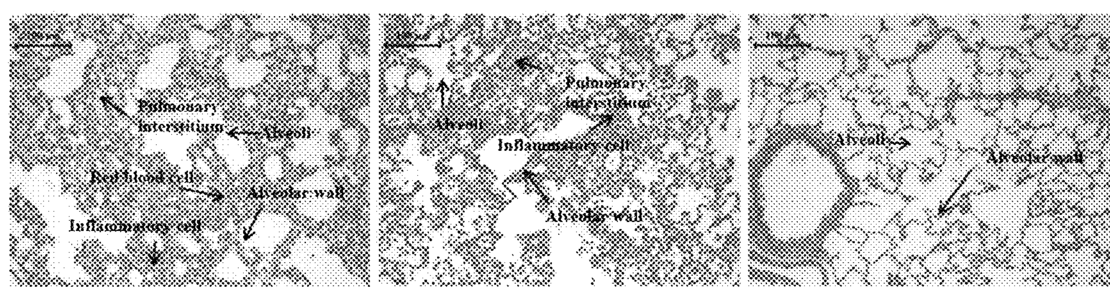
Figure 3G:
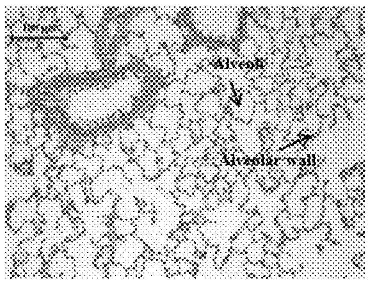

The present invention provides a use of a polypeptide in a drug for preventing and treating pneumonia.

The present invention also provides a drug for preventing and treating pneumonia. The drug includes a polypeptide, an amino acid sequence of which is SEQ ID NO: 1.

One aspect of the present invention provides a drug for preventing and treating pneumonia, an active ingredient of which includes a polypeptide.

The drug of the present invention may include the polypeptide as a sole therapeutic agent, which may alternatively be combined with another excipient, carrier, or auxiliary ingredient.

The drug of the present invention may further include one or more therapeutic agents, which may alternatively be combined with another excipient, carrier, or auxiliary ingredient.

Another aspect of the present invention provides a use of a polypeptide in a drug for preventing and treating pneumonia. The drug of the present invention is prepared from the polypeptide of the present invention as a main active ingredient, added with another pharmaceutically acceptable excipient, carrier, or auxiliary ingredient, and can be used for preventing and treating pneumonia.

Yet another aspect of the present invention provides a use of a polypeptide in a drug for preventing and treating pneumonia. The drug of the present invention is prepared from a combination of the polypeptide of the present invention and another therapeutic agent, added with another pharmaceutically acceptable excipient, carrier, or auxiliary ingredient, and can be used for preventing and treating pneumonia.

Preferably, the pneumonia includes community-acquired pneumonia.

Preferably, the preparation of the present invention further includes another excipient, carrier, or auxiliary ingredient.

A preparation of the present invention may be any one or a combination of an injection, lyophilized powder (for injection), a solid preparation, a spray, a solution, a suspension, an emulsion, a semi-solid preparation, a liquid preparation, tablets, capsules, enteric-coated tablets, pills, powder, granules, a sustained release or delayed release preparation, and the like.

The drug of the present invention may further include another pharmaceutically acceptable excipient, carrier, or auxiliary ingredient, and may be prepared into a pharmaceutically acceptable dosage form as required. The pharmaceutically acceptable excipient, carrier, or auxiliary ingredient includes a conventional diluent, excipient, filler, adhesive, wetting agent, disintegrating agent, absorption enhancer, surfactant, adsorption carrier, lubricant, or the like in the pharmaceutical field, and may be added with a fragrance agent, a sweetener, or the like when necessary.

Specifically, pharmaceutically common diluents and absorbers include, for example, starch, dextrin, calcium sulfate, lactose, mannitol, sucrose, sodium chloride, glucose, urea, calcium carbonate, kaolin, microcrystalline cellulose, and aluminum silicate. Pharmaceutically common wetting agents and adhesives include, for example, water, glycerin, polyethylene glycol, ethanol, propanol, starch slurry, dextrin, syrup, honey, glucose solution, Arabic mucilage slurry, gelatin slurry, sodium carboxymethyl cellulose, lac, methyl cellulose, potassium phosphate, and polyvinylpyrrolidone.

Pharmaceutically common disintegrating agents include, for example, dried starch, alginate, agar powder, brown algae starch, sodium bicarbonate, citric acid, calcium carbonate, polyoxyethylene, sorbitol fatty acid ester, sodium dodecyl sulfonate, methyl cellulose, and ethyl cellulose. Disintegration inhibitors include, for example, sucrose, glycerol tristearate, cocoa butter, and hydrogenated oil.

Pharmaceutically common lubricants include, for example, talc powder, silica, corn starch, stearate, boric acid, liquid paraffin, and polyethylene glycol.

Pharmaceutically common salts (in a form of water-soluble, oil-soluble, or dispersable products) include, for example, conventional nontoxic salts or quaternary ammonium salts formed from inorganic or organic acids or bases, including acid addition salts, such as acetates, adipates, alginate, aspartates, benzoates, benzenesulfonates, sulfites, butyrates, citrates, cyclopentanpropionates, disgluconates, esilates, glucoseheptanates, glycerophosphates, hemisulfates, lactates, oxalates, palmitates, pectinates, succinates, and tartrates.

Pharmaceutically acceptable carriers or excipients will not be enumerated one by one, and specific choices may be made by those of ordinary skill in the art according to mastered common general knowledge.

Preferably, the preparation of the present invention may be administered by any one or a combination of oral administration, parenteral administration, topical administration, injection administration, inhalation administration, and mucosal administration. An optimal administration route is affected by many factors, including physical and chemical properties of active molecules, urgency of clinical manifestations, and a relationship between a plasma concentration of active molecules and a desired therapeutic effect.

Preferably, the drug provided by the present invention further includes one or more therapeutic agents.

Preferably, in the drug of the present invention, the therapeutic agent includes, but is not limited to, β-lactam/β-lactamase inhibitors (penicillins, cephalosporins), fluoroquinolones (moxifloxacin, gemifloxacin, and levofloxacin), carbapenems, erythromycin, budesonide, oseltamivir, azithromycin, oseltamivir, andrographolide, kalil dehydrographolidi succinatis, or combinations thereof.

In addition, a daily dosage of these pharmaceutical preparations may be appropriately changed according to the symptom, age, weight, gender, treatment time, treatment effect, administration method, and the like of a subject, and is not specifically limited as long as influenza infection can be inhibited and side effects produced are within an allowable range. The preparation is not limited to being administered once a day, but can be administered several times.

The preparation of the present invention may be prepared by any suitable method known in the art, and may have deletion or adjustment according to requirements of a dosage form.

A person skilled in the art may select appropriate excipients according to a required dosage form and general technical knowledge and requirements of the dosage form in the art, add appropriate excipients and additives on the basis of the polypeptide, and prepare a dosage form such as tablets, powder, or liquid according to a conventional preparation technology.

A person skilled in the art may determine, in a conventional way, a preferred dose suitable for a certain case.

The polypeptide in the present invention may be chemically synthesized, and may also be obtained by expression, separation, and purification in genetic engineering technology (for a specific method, see Sambrook et al., Molecular Cloning: A Laboratory Manual, Cold Spring Harbor Laboratory Press, Cold Spring Harbor, NY, 2001).

Unless otherwise specified, the technical means used in embodiments are conventional means well known to those skilled in the art. In the embodiments, all reagents and the like added are commercially available unless otherwise specified.

Examples in this section further illustrate content of the present invention, but should not be construed as limiting the present invention. Modifications or substitutions made to the methods, steps, or conditions of the present invention fall within the scope of the present invention without departing from the spirit and essence of the present invention.

Example 1 Therapeutic Effect of Polypeptide on Infectious Pneumonia In Vivo

Bacterial pneumonia is the most common pneumonia, is also one of the most common infectious diseases, and is caused by bacterial infection. Main pathogenic bacteria of the bacterial pneumonia include *Streptococcus pneumoniae, Staphylococcus aureus, Escherichia coli*, and the like, which pose a great threat to the health of children and the elderly. In this experiment, a mixed bacteria solution of *Staphylococcus aureus, Streptococcus pneumoniae*, and *Escherichia coli* was instilled into the trachea to induce models of pneumonia in rats. Pharmacodynamic effects of a peptide on pneumonia were evaluated by observing effects of the peptide inhaled through the nose and mouth on the models of pneumonia caused by mixed bacteria infection.

Because erythromycin and budesonide are antibacterial drugs used for treating pneumonia at present, the two drugs were selected as positive reference substances. The erythromycin was produced by Dongyi Hetian Biotechnology Co., Ltd., and the budesonide was produced by AstraZeneca Co., Ltd. in Australia.

80 SD rats, SPF grade, half male and half female, were selected and randomly divided into 8 groups according to sex and body weight, including 6 rats in each of a blank control group and a model evaluation group, 8 rats in a blank administration group, and 12 rats in each of a model control group, an erythromycin group, a budesonide group, a low-dose polypeptide treatment group, and a high-dose polypeptide treatment group.

Animals in the blank administration group were not modeled, and inhaled a high-concentration polypeptide aerosol (0.48 mg/L) through nose and mouth every day. Animals in the blank control group were instilled with a 0.5 mL 0.9% sodium chloride injection through trachea. After the remaining groups were slightly anesthetized with ether, the model control group, the erythromycin group, the budesonide group, the low-dose polypeptide treatment group, and the high-dose polypeptide treatment group were instilled with a $1\times10^8$ CFU/mL mixed bacteria solution of *Staphylococcus aureus, Streptococcus pneumoniae*, and *Escherichia coli* through trachea, 0.5 mL/rat, respectively, and the blank control group was instilled with a 0.9% sodium chloride injection of a same volume.

A specific modeling method was as follows: a rat was anesthetized by ether inhalation and lied on an anatomical plate at an angle of 30-45°, trachea of the rat was exposed under an otoscope, a long puncture needle was connected to a 1 mL syringe and inserted into the trachea, each rat was injected with 0.5 mL of mixed bacteria, the puncture needle was pulled out after the injection, the rat was still kept at the original tilt position for about 10 min, and the bacteria solution flowed into bronchus and alveoli due to gravity to cause infection, so as to induce a rat pneumonia model.

A 7.16 mg/mL solution for the low-dose peptide treatment group and a 71.6 mg/mL solution for the high-dose peptide treatment group were atomized to generate aerosol particles with a drug concentration of 0.07 mg/L and aerosol particles with a drug concentration of 0.48 mg/L respectively before an experiment.

1. Verification on Concentrations of Atomized Aerosol Particles

Before first administration, the atomization of the aerosol particles was verified: aerosol particles at any exposed port were collected by using a filter membrane at a sampling flow rate of 1 L/min for 5 min, content of a tested article in the atomized aerosol solution was measured, the aerosol particles of two concentrations were collected by using Anderson samplers a sampling flow rate of 1 L/min for 3 to 5 min (5 min for a low dose, 3 min for a high dose), a median mass aerodynamic diameter (MMAD) and a standard deviation (GSD) of the polypeptide in the aerosol particles of each concentration were tested and calculated, and the concentration of aerosol particles in an administration process of each administration group was monitored by using an aerosol mass concentration tester every day. Results of content and diameter distribution of the tested article in aerosol were shown in Table 1.

TABLE 1

Content and diameter distribution of the tested article in aerosol

| Group | Content of tested article | | | Particle size distribution | | Whether qualified |
|---|---|---|---|---|---|---|
| | Target concentration | Measured concentration (mg/L) | Accuracy (%) | Median mass aerodynamic diameter (MMAD, μm) | Geometric standard deviation (GSD) | |
| Blank control group | — | — | — | — | — | — |
| Model evaluation group | — | — | — | — | — | — |
| Model control group | — | — | — | — | — | — |
| Erythromycin group | — | — | — | — | — | — |
| Budesonide group | — | — | — | — | — | — |
| Low-dose polypeptide treatment group | 0.07 | 0.0839 | 19.9 | 1.10 | 2.90 | Qualified |
| High-dose polypeptide treatment group | 0.48 | 0.4724 | 1.6 | 1.28 | 2.24 | Qualified |
| Blank administration group | 0.48 | 0.4724 | 1.6 | 1.28 | 2.24 | Qualified |

It can be seen from Table 1 that before the first administration, the polypeptide in the aerosol particles of each concentration had an MMAD of 1 to 4 μm and a GSD of 1 to 3, which met test requirements.

2. Administration Test

Each group was administrated for the first time at 2 h after modeling. After the experiment begun, 7.16 mg/mL and 71.6 mg/mL peptide solutions were atomized into aerosol particles with target concentrations of 0.07 and 0.48 mg/L every day, and the animals in the low-dose peptide treatment group and the high-dose peptide treatment group (0.54 mg/kg and 3.7 mg/kg, corresponding to drug concentrations 0.07 and 0.48 mg/L respectively) inhaled the aerosol particles with corresponding concentrations through mouth and nose respectively for 7 consecutive days, 10 min/time, 3 times a day; the blank administration group (cumulative dose 22.2 mg/kg, corresponding to a drug concentration 0.48 mg/L) inhaled 0.48 mg/L peptide aerosol particles through mouth and nose every day for 7 consecutive days, 20 min/time, 3 times a day; the blank control group and the model control group inhaled a 0.9% sodium chloride solution for the same time according to the same method; the erythromycin group and the budesonide group were administrated with a 5 mg/mL erythromycin solution and a 0.05 mg/mL budesonide suspension respectively for the same time according to the same method; and body weight of each group was tested every day.

2.1 Verification on Model Animals

At 24 h after the mixed bacteria solution of *Staphylococcus aureus, Streptococcus pneumoniae*, and *Escherichia coli* was instilled through the trachea, in order to verify modeling success, 6 animals in the model evaluation group were dissected, lungs were taken out, fixed in formalin, embedded, sectioned, and stained with HE, and pathological changes of lungs were observed under a light microscope. It was regarded as success that the lungs of at least 5 of 6 rats had obvious pathological changes. Results showed that pathological changes such as damage of an alveolar structure, obvious thickening of an alveolar wall, hyperemia of alveolar wall blood vessels, and infiltration of mass inflammatory cells occurred in all the 6 animals, indicating a success in the models of rat pneumonia induced by the mixed bacteria instilled through the trachea. This batch of model animals may be used for follow-up tests. See FIGS. 1A-IF for specific pathological changes of lungs.

FIGS. 1A-IF showed pathological changes such as hyperemia of alveolar wall blood vessels, thickening of an alveolar wall, damage of an alveolar structure, and infiltration of mass inflammatory cells. Pathological scores were 3.0±0.6.

2.2 Lung Function Test, Gross Anatomy Examination, and Pathological Test 2.2.1 Experimental Design Except the blank administration group, half animals of the remaining groups were randomly selected for lung function test, gross anatomy examination, and pathological test on D4 day, and lungs of 3 animals in each group were selected for bacteria culture and counting; and on D8 day, the remaining animals were subjected to lung function test, gross anatomy examination, and pathological test, and lungs of 3 animals in each group were selected for bacteria culture and counting (the blank control group and the blank administration group were not examined).

2.2.2 Test Steps 2.2.2.1 Gross Anatomical Examination and Pathological Test

Experimental steps of gross anatomical examination and pathological test: the rats to be tested were anesthetized by intraperitoneal injection of 20% ethyl carbamate (dose 1000 mg/kg), and lung functions of the rats in each group were first tested with a lung function tester. Blood was collected from a ventral aorta, partial pressure of oxygen ($PaO_2$) and partial pressure of carbon dioxide ($PaCO_2$) in the blood of the rats were measured by using a blood gas analyzer, then left lower lobe lung tissues were taken, fixed in formalin, embedded, sectioned, and stained with HE, and pathological changes were observed under the light microscope.

2.2.2.2 Bacteria Counting

Experimental steps of bacteria culture: except the blank administration group, six animals were randomly selected from each of the remaining groups (three animals were randomly selected from the first and last anatomies), left middle lobe lung tissues were taken, washed with 0.9% sodium chloride injection, added with double weight of 0.9% sodium chloride injection, and ground into homogenate, the homogenate was inoculated into a meat extract agar medium and cultured at 37° C. for 16 to 18 h, bacteria were isolated, and each isolated bacteria suspension was diluted to $10^{-1}$, $10^{-2}$, $10^{-3}$, $10^{-4}$, $10^{-3}$, $10^{-6}$, $10^{-7}$ and $10^{-8}$ according to 10 times gradient, namely, 9 mL normal saline plus 1 mL bacteria suspension was $10^{-1}$, and so on. 0.1 mL of bacteria suspension with proper concentration was selected and put on a selective culture medium, the bacteria suspension was gently pushed away and cultured for 24 h to 48 h, then bacteria were counted with a bacteria counter, and the number of bacteria per mL bacteria suspension was calculated according to its dilution concentration. Compared with the model control group, an inhibition rate of each group was calculated.

2.2.3 Test Results and Analysis

Experimental data and results were as follows:

(1) See Table 2 for Effects of Each Test Group on Rat Lung Functions in Different Stages.

Compared with the model control group, the tidal volume (VT) showed an increasing trend and the respiratory rate (f) showed a decreasing tread (tended to normal) on D4 day in the erythromycin group, the budesonide group, the low-dose polypeptide treatment group, and the high-dose polypeptide treatment group, but there was no significant difference; and there was no significant change in minute ventilation (MV). Compared with the model control group, FVC, FEV200 and FEV200/FVC in the high-dose polypeptide treatment group increased significantly, and FEV200/FVC in the erythromycin group and the low-dose polypeptide treatment group increased significantly.

Compared with the model control group, f, MV, FVC, and FEV200 showed increasing rising trends in the erythromycin group, the budesonide group, the low-dose polypeptide treatment group, and the high-dose polypeptide treatment group on D8 day, but there was no statistical difference. Compared with the model control group, the tidal volumes in the erythromycin group, the budesonide group, the low-dose polypeptide group, and the high-dose polypeptide group increased significantly, and the FEV200/FVC in the erythromycin group, the low-dose polypeptide group, and the high-dose polypeptide group increased significantly. There was no significant difference in VT, f, MV, FVC, FEV200, and FEV200/FVC between the blank administration group and the blank control group. Compared with the erythromycin group, VT, f, MV, FVC, FEV200, and FEV200/FVC in the low-dose polypeptide treatment group

TABLE 2

Effects of each test group on rat lung functions in different administration stages

| Administration stage | Test index (unit) | Blank control group | Model control group | Erythromycin group | Budesonide group | Low-dose polypeptide treatment group | High-dose polypeptide treatment group | Blank administration group |
|---|---|---|---|---|---|---|---|---|
| D4 | VT (mL) | 1.77 ± 0.35 | 1.41 ± 0.43 | 1.59 ± 0.39 | 1.86 ± 0.69 | 1.78 ± 0.69 | 1.93 ± 0.62 | — |
| | f (time/min) | 112 ± 26 | 153 ± 31 | 132 ± 27 | 130 ± 39 | 130 ± 41 | 116 ± 24 | — |
| | MV (mL) | 0.19 ± 0.02 | 0.21 ± 0.03 | 0.20 ± 0.02 | 0.22 ± 0.04 | 0.21 ± 0.04 | 0.21 ± 0.04 | — |
| | FVC (mL) | 4.02 ± 0.35 | 2.77 ± 0.26$^{+}$ | 3.12 ± 0.52 | 3.13 ± 0.59 | 2.98 ± 0.24 | 3.59 ± 0.82* | — |
| | FEV200 (mL) | 3.74 ± 0.31 | 2.21 ± 0.26 | 2.84 ± 0.54 | 2.72 ± 0.72 | 2.73 ± 0.27 | 3.25 ± 0.88** | — |
| | FEV200/FVC (%) | 93.31 ± 0.77 | 79.96 ± 6.16 | 90.65 ± 4.78** | 85.78 ± 8.00 | 91.51 ± 3.83** | 89.98 ± 7.96* | — |
| D8 | VT (mL) | 1.78 ± 0.23 | 1.22 ± 0.22$^{++}$ | 1.67 ± 0.24** | 1.63 ± 0.27** | 1.68 ± 0.28** | 1.67 ± 0.21** | 1.76 ± 0.25 |
| | f (time/min) | 116 ± 10 | 125 ± 15 | 130 ± 25 | 126 ± 11 | 118 ± 19 | 121 ± 18 | 116 ± 15 |
| | MV (mL) | 0.21 ± 0.03 | 0.15 ± 0.01 | 0.21 ± 0.01 | 0.21 ± 0.04 | 0.20 ± 0.05 | 0.20 ± 0.03 | 0.20 ± 0.04 |
| | FVC (mL) | 4.75 ± 1.89 | 3.55 ± 0.45 | 3.68 ± 0.20 | 3.80 ± 0.65 | 3.68 ± 0.71 | 3.58 ± 0.58 | 4.01 ± 1.08 |
| | FEV200 (mL) | 4.43 ± 1.70 | 2.93 ± 0.63 | 3.40 ± 0.12 | 3.43 ± 0.69 | 3.43 ± 0.72 | 3.27 ± 0.46 | 3.77 ± 1.07 |
| | FEV200/FVC (%) | 93.58 ± 1.50 | 81.63 ± 7.70$^{+}$ | 92.36 ± 2.94** | 89.77 ± 4.58 | 92.88 ± 2.40** | 91.86 ± 3.49* | 93.81 ± 3.03 |

Note:
compared with the blank control group, $^{+}P \leq 0.05$, and $^{++}P \leq 0.01$; and compared with the model control group, $^{*}P \leq 0.05$, and $^{**}P \leq 0.01$
VT: tidal volume;
f: respiratory rate;
MV: minute ventilation;
FVC: forced vital capacity;
FEV: Forced expiratory volume As shown in Table 2, compared with the blank control group, the forced vital capacity (FVC) on D4 day, the tidal volume on D8 day, and the FEV200/FVC decreased significantly and the respiratory rate (F) on D4 increased by 37% in the model control group, indicating that due to the limited ventilation function of lungs in the early stage of pneumonia, the body maintained a constant ventilation by increasing the respiratory rate.

and the high-dose polypeptide treatment group had no statistical difference on D4 day, but in the high-dose polypeptide group, the VT, FVC, and FEV200 showed increasing trends compared with the erythromycin group and the budesonide group, and the respiratory rate showed a decreasing trend compared with the erythromycin group and the budesonide group. VT, f, MV, FVC, FEV200, and FEV200/FVC in the low-dose polypeptide treatment group and the high-dose polypeptide treatment group on D8 day were similar to those in the erythromycin group and the budesonide group, and there was no increasing or decreasing trend.

Therefore, the high-dose peptide treatment group showed better efficacy than erythromycin and budesonide on D4 day, but there was no difference in efficacy on D8 day, indicating that the onset time of 3.7 mg/kg peptide was earlier than that of 18 mg/kg erythromycin and 0.18 mg/kg budesonide.

(2) Effects of Different Test Groups on Arterial Blood Gas of Rats were Shown in Table 3.

TABLE 3

Effects of each test group on arterial blood gas of rats

| Group | D4 | | | D8 | | |
|---|---|---|---|---|---|---|
| | pH | $PaCO_2$ (mmHg) | $PaO_2$ (mmHg) | pH | $PaCO_2$ (mmHg) | $PaO_2$ (mmHg) |
| Blank control group | 7.40 ± 0.04 | 33.73 ± 2.81 | 92.90 ± 22.36 | 7.36 ± 0.04 | 44.25 ± 3.61 | 105.95 ± 1.06 |
| Model control group | 7.17 ± 0.14$^{+}$ | 72.25 ± 21.06$^{+}$ | 64.88 ± 20.78 | 7.24 ± 0.16 | 60.88 ± 21.43 | 51.82 ± 12.88$^{++}$ |
| Erythromycin group | 7.33 ± 0.05* | 50.38 ± 6.60* | 69.68 ± 15.16 | 7.42 ± 0.04 | 39.37 ± 5.60** | 71.08 ± 14.74 |
| Budesonide group | 7.31 ± 0.07 | 52.87 ± 13.34 | 75.73 ± 30.92 | 7.45 ± 0.06 | 34.35 ± 8.17** | 86.67 ± 24.78** |
| Low-dose polypeptide treatment group | 7.33 ± 0.04* | 44.63 ± 7.21* | 65.00 ± 15.59 | 7.43 ± 0.03 | 37.88 ± 6.95** | 86.85 ± 32.62** |
| High-dose polypeptide treatment group | 7.33 ± 0.05* | 46.12 ± 6.15** | 77.57 ± 16.62 | 7.43 ± 0.05 | 39.38 ± 8.14** | 78.52 ± 15.75* |
| Blank administration group | — | — | — | 7.46 ± 0.04 | 33.09 ± 8.33 | 82.77 ± 11.87 |

Note:
compared with the blank control group, $^{+}P \leq 0.05$, and $^{++}P \leq 0.01$; and compared with the model control group, $^{*}P \leq 0.05$, and $^{**}P \leq 0.01$
$PaCO_2$: partial pressure of carbon dioxide;
$PaO_2$: partial pressure of oxygen As shown in Table 3, compared with the blank control group, pH decreased significantly, $PCO_2$ increased significantly, and $PaO_2$ decreased by 30.16% in the arterial blood of the model control group on D4 day, but there was no statistical difference. Compared with the model control group, on D4 day, $PO_2$ increased to a certain extent in the erythromycin group, the budesonide group, the low-dose polypeptide treatment group, and the high-dose polypeptide treatment group, but there was no statistical difference; and pH increased significantly and $PaCO_2$ decreased significantly in the arterial blood of the low-dose polypeptide treatment group and the high-dose polypeptide treatment group, while pH showed an increasing trend and $PaCO_2$ showed a decreasing trend in the budesonide group, but there was no statistical difference.

Compared with the blank control group, on D8 day, pH and $PaCO_2$ had no statistical difference but $PaO_2$ decreased significantly in the arterial blood of the model control group; and pH, $PaCO_2$, and $PaO_2$ in the blank administration group were not significantly different from those in the blank control group, indicating that a cumulative dose of 22.2 mg/kg peptide inhaled through nose and mouth for 7 consecutive days had no obvious effect on pH, $PaCO_2$, and $PaO_2$ in the blood of rats. Compared with the model control group, on D8 day, pH showed an increasing trend in the erythromycin group, the budesonide group, the low-dose polypeptide treatment group, and the high-dose polypeptide treatment group, but there was no statistical difference; and $PaCO_2$ decreased significantly in the arterial blood of the erythromycin group, the budesonide group, the low-dose polypeptide treatment group, and the high-dose polypeptide treatment group, $PaO_2$ increased significantly in the budesonide group, the low-dose polypeptide treatment group, and the high-dose polypeptide treatment group, and $PaO_2$ increased by 37.17% in the erythromycin group (vs model control group), but there was no statistical difference.

Compared with the erythromycin group, pH, $PaCO_2$, and $PaO_2$ were not significantly different in the blood of rats in the low-dose polypeptide treatment group and the high-dose polypeptide treatment group on D4 and D8 days. Compared with the budesonide group, pH, $PaCO_2$, and $PaO_2$ were not significantly different in the blood of rats in the low-dose polypeptide treatment group and the high-dose polypeptide treatment group on D4 and D8 days.

The above data showed that polypeptide, erythromycin, and budesonide can significantly regulate the pH, $PaCO_2$, and $PaO_2$ in the arterial blood of rats with bacterial pneumonia, and the efficacy of the low-dose polypeptide (0.54 mg/kg) was equivalent to that of the erythromycin solution (18 mg/kg) and the budesonide suspension (0.18 mg/kg).

(3) Pathological Study on Rat Lungs on D4 and D8

As can be seen from FIGS. 2A-2F and FIGS. 3A-3G, there was no obvious abnormality in the lungs of the blank control group. On D4 day, the model control group showed damage of an alveolar structure, significant thickening of an alveolar wall, hyperemia in visible alveolar wall blood vessels, and infiltration of mass inflammatory cells. On D4 day, the erythromycin group, the budesonide group, the low-dose polypeptide treatment group, and the high-dose polypeptide treatment group showed thickening of an alveolar wall, slight hyperemia in alveolar wall blood vessels, infiltration of inflammatory cells, and abnormality of an alveolar structure. The pathological changes were significantly alleviated compared with the model control group.

On D8 day, the model control group showed obvious thickening of an alveolar wall, little hyperemia in visible alveolar wall blood vessels, and infiltration of mass inflammatory cells. On D8 day, lung tissue lesions in the erythromycin group, the budesonide group, the low-dose polypeptide treatment group, and the high-dose polypeptide treatment group were alleviated significantly, where lung tissues in the erythromycin group and the high-dose polypeptide treatment group tended to normal. Lung tissue microscopy showed no obvious abnormality in the blank administration group, indicating that the cumulative dose of 22.2 mg/kg polypeptide aerosol inhaled through nose and mouth did not show any pathological change related to the tested article.

(4) the Number of Bacteria in Lung Tissues of Pneumonia Model Rats in Each Test Group was Shown in Table 4.

TABLE 4

Number of bacteria in lung tissues of pneumonia model rats in each test group

| Test stage | Test index (unit) | Model control group | Erythromycin group | Budesonide group | Low-dose polypeptide treatment group | High-dose polypeptide treatment group |
|---|---|---|---|---|---|---|
| D4 | Number of *escherichia coli* (CFU/mL) | 3100 ± 544 | 447 ± 146 | 3737 ± 1115 | 893 ± 155 | 243 ± 101 |
| | Number of *staphylococcus aureus* (CFU/mL) | 5027 ± 1017 | 633 ± 146 | 2577 ± 655 | 977 ± 211 | 453 ± 92 |
| | Number of *streptococcus pneumoniae* (CFU/mL) | 4730 ± 1062 | 1223 ± 287 | 1810 ± 957 | 750 ± 125 | 450 ± 82* |
| | Inhibition rate of *escherichia coli* (%) | — | 85.58 | −20.55 | 71.19 | 92.16 |
| | Inhibition rate of *staphylococcus aureus* (%) | — | 87.41 | 48.74 | 80.56 | 90.99 |
| | Inhibition rate of *streptococcus pneumoniae* (%) | — | 74.14 | 61.73 | 84.14 | 90.49 |
| D8 | Number of *escherichia coli* (CFU/mL) | 963 ± 110 | 80 ± 2* | 890 ± 409 | 137 ± 81** | 33 ± 42* |
| | Number of *staphylococcus aureus* (CFU/mL) | 3380 ± 1434 | 113 ± 31 | 560 ± 269 | 110 ± 36 | 87 ± 64 |
| | Number of *streptococcus pneumoniae* (CFU/mL) | 1583 ± 166 | 67 ± 15* | 433 ± 276 | 80 ± 30* | 20 ± 10* |
| | Inhibition rate of *escherichia coli* (%) | — | 91.69 | 7.58 | 85.77 | 96.57 |
| | Inhibition rate of *staphylococcus aureus* (%) | — | 96.66 | 83.43 | 96.75 | 97.43 |
| | Inhibition rate of *streptococcus pneumoniae* (%) | — | 95.77 | 72.65 | 94.95 | 98.74 |

Note:
compared with the model control group, *P ≤ 0.05, and ** P ≤ 0.01

As shown in Table 4, compared with the model control group, on D4 day, the numbers of *Escherichia coli, Staphylococcus aureus*, and *Streptococcus pneumoniae* decreased greatly in the lung tissues of animals in each administration group, but only the number of *Streptococcus pneumoniae* in the high-dose polypeptide treatment group decreased significantly compared with the model control group ($P<0.05$), and there was no statistical difference in the number of bacteria in the lungs of the remaining groups. In addition, each administration group had different inhibition rates against *Escherichia coli, Staphylococcus aureus*, and *Streptococcus pneumoniae*, where the inhibition rates against *Escherichia coli* were 85.58%, 71.19% and 92.16% in the erythromycin group, the low-dose polypeptide treatment group, and the high-dose polypeptide treatment group respectively, while the inhibition rate of budesonide against *Escherichia coli* was −20.55%. In the erythromycin group, the budesonide group, the low-dose polypeptide treatment group, and the high-dose polypeptide treatment group, the inhibition rates against *Staphylococcus aureus* were 87.41%, 48.74%, 80.56%, and 90.99%, respectively; and the inhibition rates against *Streptococcus pneumoniae* were 74.14%, 61.73%, 84.14% and 90.49%, respectively.

Compared with the model control group, on D8 day, the numbers of *Escherichia coli, Staphylococcus aureus*, and *Streptococcus pneumoniae* showed decreasing trends in the lungs of animals in the budesonide group, but there was no statistical difference; the number of *Staphylococcus aureus* decreased greatly in the lungs of animals in the erythromycin group, the low-dose polypeptide treatment group, and the high-dose polypeptide treatment group, but there was no statistical difference; and the numbers of *Escherichia coli* and *Streptococcus pneumoniae* decreased significantly in the lungs of the erythromycin group, the low-dose polypeptide group, and the high-dose polypeptide group ($P<0.05$ or $P<0.01$). On D8, in the erythromycin group, the budesonide group, the low-dose polypeptide treatment group, and the high-dose polypeptide treatment group, the inhibition rates against *Escherichia coli* were 91.69%, 7.58%, 85.77%, and 96.57%, respectively; the inhibition rates against *Staphylococcus aureus* were 96.66%, 83.43%, 96.75%, and 97.43%, respectively; and the inhibition rates against *Streptococcus pneumoniae* were 95.77%, 72.65%, 94.95%, and 98.74%, respectively.

Compared with the erythromycin group, *Escherichia coli, Staphylococcus aureus*, and *Streptococcus pneumoniae* showed decreasing trends in the lungs of animals in the high-dose polypeptide treatment group on D4 and D8, but there was no statistical difference; and compared with the budesonide group, *Escherichia coli, Staphylococcus aureus*, and *Streptococcus pneumoniae* showed decreasing trends in the lungs of animals in the low-dose polypeptide treatment group and the high-dose polypeptide treatment group on D4 and D8, but there was no statistical difference, indicating that the inhibiting effects of the high-dose polypeptide treatment group (3.7 mg/kg) on *Escherichia coli, Staphylococcus aureus*, and *Streptococcus pneumoniae* were better than those of the erythromycin solution (18 mg/kg) and the budesonide suspension (0.18 mg/kg).

By analysis on the foregoing results, erythromycin, budesonide, and polypeptide administrated by oral and nasal inhalation can significantly inhibit replication of *Staphylococcus aureus* and *Streptococcus pneumoniae* in lung tissues, whereas the budesonide had no significant inhibiting effect on *Escherichia coli* in the lungs of rats with bacterial infection, and at the same time, the high-dose polypeptide treatment group (3.7 mg/kg) had better efficacy than the erythromycin solution (18 mg/kg) and the budesonide suspension (0.18 mg/kg).

3. During the experiment, body weight of rats was recorded every day, as shown in FIG. 4 for details.

Figure 4:
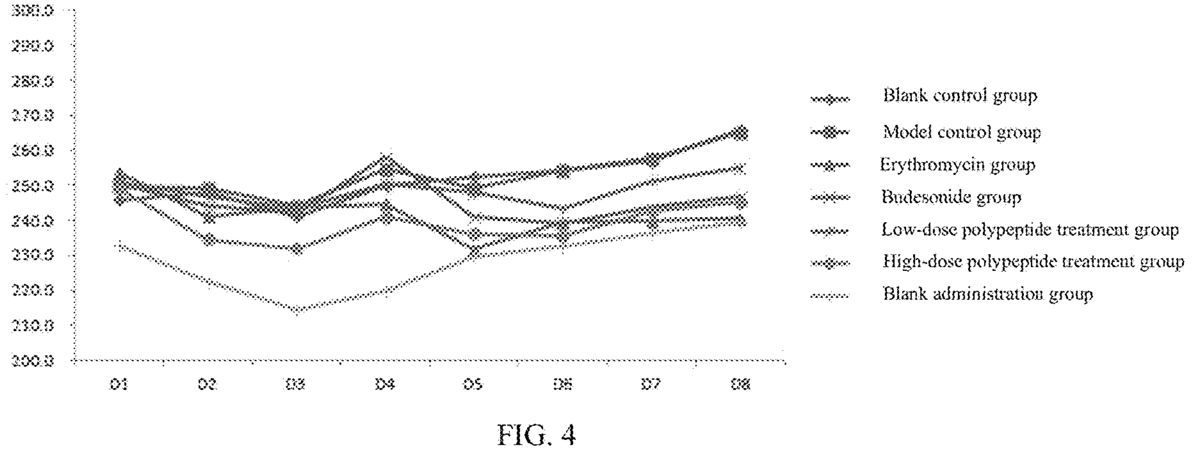
FIG. 4 is a diagram of weight changes of rats in each test group during test.

As can be seen from FIG. 4, compared with the blank control group, there was no significant difference in body weight of the model control group; compared with the model control group, there was no significant difference in the erythromycin group, the budesonide group, the low-dose polypeptide treatment group, and the high-dose polypeptide treatment group; and compared with the blank control group, there was no significant difference in body weight of the blank administration group.

Therefore, administrations of the low-dose polypeptide treatment group and the high-dose polypeptide treatment group did not affect the body weight of rats.

To sum up, the polypeptide administrated by nose and mouth inhalation had a significant therapeutic effect on bacterial pneumonia induced by mixed bacteria, and the results of the high-dose polypeptide treatment group were better than those of the erythromycin group and the budesonide group.

At the same time, SD rats inhaled 22.2 mg/kg polypeptide solution through nose and mouth for 7 consecutive days, showing that no related pathological changes occurred in lung tissues, and there was no significant difference in lung function indexes, and WBC, Neu, TNF-$\alpha$, and IL-6 in alveolar lavage fluid compared with the blank control group.

In addition, the polypeptide of the present invention is composed of 19 amino acids, and degradation products are natural amino acids, so no drug residue is produced. Meanwhile, according to a sterilization mechanism, the polypeptide carries strong positive charges, the positive charges are adsorbed to surfaces of bacteria, local potentials of cell walls change suddenly to form a high potential difference, the high potential difference finally breaks down the cell walls to form holes, and when polypeptide molecules accumulate to a certain amount, the formed holes are further expanded, which destroys the integrity of cell membranes, thereby causing outflow of intracellular substances and death of bacteria. The unique sterilization mechanism determines that the polypeptide is less liable to produce drug resistance, so the polypeptide has good advantages and broad application prospects.

Herein, "drug", "pharmaceutical preparation", and "preparation" may be used interchangeably unless specifically stated, and refer to articles containing active ingredients of drugs, and optionally further containing pharmaceutically acceptable carriers. "Pharmaceutically acceptable" means that a substance or a composition shall be chemically and/or toxicologically compatible with another ingredient containing a preparation and/or a mammal treated with the substance or the composition. A "pharmaceutically acceptable carrier" refers to a non-toxic, solid, semi-solid, or liquid filler, diluent, excipient, wrapping material, or another pharmaceutical adjunct. The carrier used may be adapted to a corresponding administration form. The carrier known to those skilled in the art may be used to prepare any one or a combination of an injection, lyophilized powder (for injection), a solid preparation, a spray, a solution, a suspension, a semi-solid preparation, a liquid preparation, tablets, capsules, enteric-coated tablets, pills, powder, granules, a sustained release or delayed release preparation, and the like.

The foregoing descriptions are merely embodiments of the present invention, and do not therefore limit the patent scope of the present invention. Any equivalent structures or equivalent process transformations made by using content of the specification of the present invention, or directly or indirectly used in other related technical fields, are likewise included in the patent protection scope of the present invention.

What is claimed is:

1. A method of treating bacterial pneumonia caused by a bacterial infection, the method comprising administering an aerosol three times per day for 10 minutes for seven consecutive days by inhalation to a subject in need thereof, wherein the aerosol comprises a polypeptide having the amino acid sequence of SEQ ID NO: 1, the aerosol is generated by atomizing a 71.6 mg/mL solution of the polypeptide to provide an aerosol concentration of 0.48 mg/L, wherein the median mass aerodynamic diameter (MMAD) of the aerosol is 1~4 μm, and the geometric standard deviation (GSD) of the aerosol is 1-3, and wherein the bacterial infection comprises a *Streptococcus pneumoniae* infection and/or an *Escherichia coli* infection, and a daily inhaled dose of the polypeptide is 3.7 mg/kg.

2. The method of claim 1, wherein the aerosol is inhaled through the mouth and nose.

3. The method of claim 1, wherein the aerosol further comprises a pharmaceutically acceptable excipient, carrier, or auxiliary ingredient.

4. The method of claim 1, further comprising co-administering one or more therapeutic agents selected from β-lactam/β-lactamase inhibitors, fluoroquinolones, carbapenems, erythromycin, budesonide, oseltamivir, azithromycin, andrographolide, kalii dehydrographolidi succinas, and combinations thereof.

5. The method of claim 1, wherein the bacterial pneumonia is community-acquired pneumonia.

6. The method of claim 1, wherein the bacterial infection is a *Streptococcus pneumoniae* infection.

* * * * *

SEQUENCE LISTING

<160> NUMBER OF SEQ ID NOS: 1

<210> SEQ ID NO 1
<211> LENGTH: 19

```
<212> TYPE: PRT
<213> ORGANISM: Artificial Sequence
<220> FEATURE:
<223> OTHER INFORMATION: The sequence is synthetized.

<400> SEQUENCE: 1

Met Gly Arg Phe Lys Arg Phe Arg Lys Lys Phe Lys Lys Leu Phe Lys
1               5                   10                  15

Lys Leu Ser
```